US00PP17277P2

(12) United States Plant Patent
Austin

(10) Patent No.: US PP17,277 P2
(45) Date of Patent: Dec. 12, 2006

(54) SHRUB ROSE PLANT NAMED 'AUSNOTICE'

(50) Latin Name: *Rosa Hybrida*
Varietal Denomination: AUSnotice

(75) Inventor: David C. H. Austin, Wolverhampton (GB)

(73) Assignee: David Austin Roses Limited, Wolverhampton (GB)

( * ) Notice: Subject to any disclaimer, the term of this patent is extended or adjusted under 35 U.S.C. 154(b) by 0 days.

(21) Appl. No.: 11/048,989

(22) Filed: Feb. 1, 2005

(51) Int. Cl.
*A01H 5/00* (2006.01)

(52) U.S. Cl. ..... Plt./107
(58) Field of Classification Search ..... Plt./107, Plt./102, 130, 137, 138, 141, 148, 149
See application file for complete search history.

*Primary Examiner*—Howard J. Locker
(74) *Attorney, Agent, or Firm*—Klarquist Sparkman LLP

(57) ABSTRACT

Shrub rose plant suitable for cut flower production in greenhouse conditions, substantially as herein shown and described, characterized particularly by its upright growth and quartered blooms of medium-pink color and strong fruity fragrance.

1 Drawing Sheet

Genus and species: *Rosa hybrida.*
Variety denomination: 'AUSnotice'.

ORIGIN OF THE INVENTION

The present invention relates to a new and distinct variety of a shrub rose plant named 'AUSnotice' which was originated by me by crossing an unnamed, unpatented seedling with an unnamed, unpatented seedling.

BACKGROUND OF THE INVENTION

The primary objective of this breeding was to produce a rose plant suitable for year round cut flower production under standard greenhouse conditions having medium pink blooms with a strong fragrance and long vase life, produced on strong, upright stems.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Quartered blooms of medium-pink color.
2. Upright growth.
3. Strong fruity fragrance.
4. Suitable for cut flower production under greenhouse conditions.

Asexual reproduction of this new variety by budding, as performed at Albrighton, England, shows that the foregoing and all other characteristics and distinctions come true to form and are established and transmitted through succeeding propagations.

Comparison with Parents

'AUSnotice' has medium-pink blooms which differ from the cream colored blooms of both the seed and pollen parents.

Comparison with Similar Variety

'AUSmary' produces deeply cupped blooms with an Old Rose fragrance, whereas the blooms of 'AUSnotice' have shallower cups and a fruity fragrance.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling (Unpatented).
*Pollen parent.*—Unnamed Seedling. (Unpatented).

FLOWER

Observations made from plants commencing at two years of age grown in a greenhouse environment at Albrighton, England.

Blooming habit: Continuous.

Bud:
*Size.*—About 3 cm long and 1.6 cm in diameter when the petals start to unfurl.
*Form.*—The bud form is pointed ovoid.
*Color.*—When sepals first divide, bud color is Red Group 47A. When half blown, the upper sides of the petals are Red Group 55A; and the lower sides of the petals are Red Group 55B.
*Sepals.*—Color: Upper surface: Yellow-Green Group 144B with Greyed-Purple Group 185A at base. Lower surface: Yellow-Green Group 144D with Yellow-Green Group 146D in center at base. Length:

2.8 cm. Width: 0.8 cm. Shape: Subulate. Surface texture: Upper surface: Smooth. Lower surface: Smooth. There is one lightly appendaged sepal[s]. There are four unappendaged sepals with canescent and slightly glandular edges.

*Receptacle.*—Color: Yellow-Green Group 144B. Shape: Campanulate. Size: Medium, about 1.2 cm long×1.1 cm wide. Surface: Smooth.

*Peduncle.*—Length: Long, averaging about 7 cm. Surface: Prickly. Color: Green Group 143A. Strength: Strong.

Bloom:

*Size.*—Large. Average open diameter is about 10.3 cm.

*Borne.*—In corymb shaped clusters of two to three blooms. For cut flower production buds may be nipped out to leave a single bloom.

*Flowering stems.*—Strength: Strong. Average length is about 50 cm with a diameter of 6 mm. Number: Usually 18.

*Form.*—When first open: Cupped. Permanence: Retains its form to the end.

*Petalage.*—Number of petals under normal conditions: 60.

*Color.*—The upper sides of the petals are Red Group 55B. The reverse sides of the petals are Red Group 54D. The bases of the petals are White Group 155B with Yellow Group 8B at center. The major color on the upper side is Red Group 55B.

*Variegations.*—None.

*Discoloration.*—The general tonality at the end of the first day: Red Group 55B. At the end of the third day: Red Group 55B (no change).

*Fragrance.*—Strong, fruity.

Petals:

*Texture.*—Satiny, thick.

*Size.*—Width: 4.6 cm. Length: 4.8 cm.

*Surface.*—Smooth.

*Shape.*—Obdeltoid. Margin. Entire and heavily undulating. Apex Shape: Obtuse. Base Shape: Rounded on outer petals, pointed on inner petals. Form: Outer petals are flat, inner petals are incurved.

*Arrangement.*—Quartered.

*Petaloids.*—Number: 2. Color: Red Group 51A.

*Persistence.*—Petals drop off cleanly before drying.

*Lastingness.*—On the plant: Long (about 6–8 days). As a cut flower: Long (about 6–8 days).

Reproductive parts:

*Stamens.*—Number: 33. Length: 10 mm. Anthers: Length: 3 mm. Color: Yellow-Orange Group 17B. Arrangement: Mixed with petaloids. Filaments: Color: Greyed-Yellow Group 1D. Length: 7 mm. Pollen: Color: Yellow-Orange Group 17B.

*Pistils.*—Number: 49. Length: 11 mm. Styles: Color: Green-Yellow Group 1C. Length: 9 mm. Stigmas: Color: Yellow Group 9B with Red Group 50B at base. Length: 2 mm.

*Hips.*—None observed.

PLANT

*Form.*—Shrub.

*Growth.*—Vigorous, upright, bushy.

*Age at maturity.*—One and one-half years.

*Mature plant.*—Height: 1 m. Width: 0.5 m.

*Rootstock.*—*Rosa multiflora inermis* for the observed plants in the United Kingdom.

Foliage: Number of leaflets on normal mid-stem leaves: 5 including terminal leaflet.

*Size.*—Large. About 16.3 cm long×13.8 cm wide.

*Quantity.*—Normal. Average number leaves per flowering stem: 7.

*Color.*—New foliage: Upper side: Yellow-Green Group 146B with red tint on margin. Lower side: Yellow-Green Group 146C overlaid with Greyed-Purple Group 183C which becomes stronger toward the margin. Old foliage: Upper side: Green Group 139A. Lower side: Yellow-Green Group 147B.

*Upper surfaces of both new and mature foliage.*—Semi-Glossy.

Leaflets:

*Size.*—About 8.1 cm long×5.5 cm wide.

*Shape.*—Broadly oval.

*Base shape.*—Rounded.

*Apex shape.*—Acuminate.

*Texture.*—Smooth.

*Edge.*—Smooth.

*Serrations.*—Single.

*Petiole.*—Color: Yellow-Green Group 144B.

*Petiole rachis.*—Color: Yellow-Green Group 144B. Underside: With prickles.

*Auricle shape.*—Subulate.

*Stipules.*—Length: 1.8 cm, glandular.

*Disease resistance.*—Resistant to mildew, blackspot and rust in greenhouse with average day temperature maintained at 17.5 degrees C.

*Pest resistance.*—Not tested.

*Vein color.*—Greyed-Orange Group 173A.

*Venation pattern.*—Reticulate.

Wood:

*New wood.*—Color: Grey-Brown Group 199A. Bark: Smooth.

*Old wood.*—Color: Yellow-Green Group 144A. Bark: Smooth.

*Internode distance.*—6 cm.

Prickles:

*Quantity.*—On main canes from base: Ordinary, 8 per 5 cm stem length. On laterals from main canes: Few, 7 per 30 cm per stem length.

*Form.*—Hooked downward.

*Length.*—9 mm.

*Color when young.*—Yellow-Green Group 152B with Grey-Brown Group N199D at tip.

*Color when mature.*—Yellow-Green Group 152B with Grey-Brown Group N199D at tip.

Small prickles:

*Quantity.*—On main stalks: None. On laterals: None.

Winter hardiness: Not tested.

I claim:

1. A new and distinct variety of rose plant of the shrub class suitable for cut flower production in greenhouse conditions, substantially as herein shown and described, characterized particularly by its upright growth and quartered blooms of medium-pink color and strong fruity fragrance.

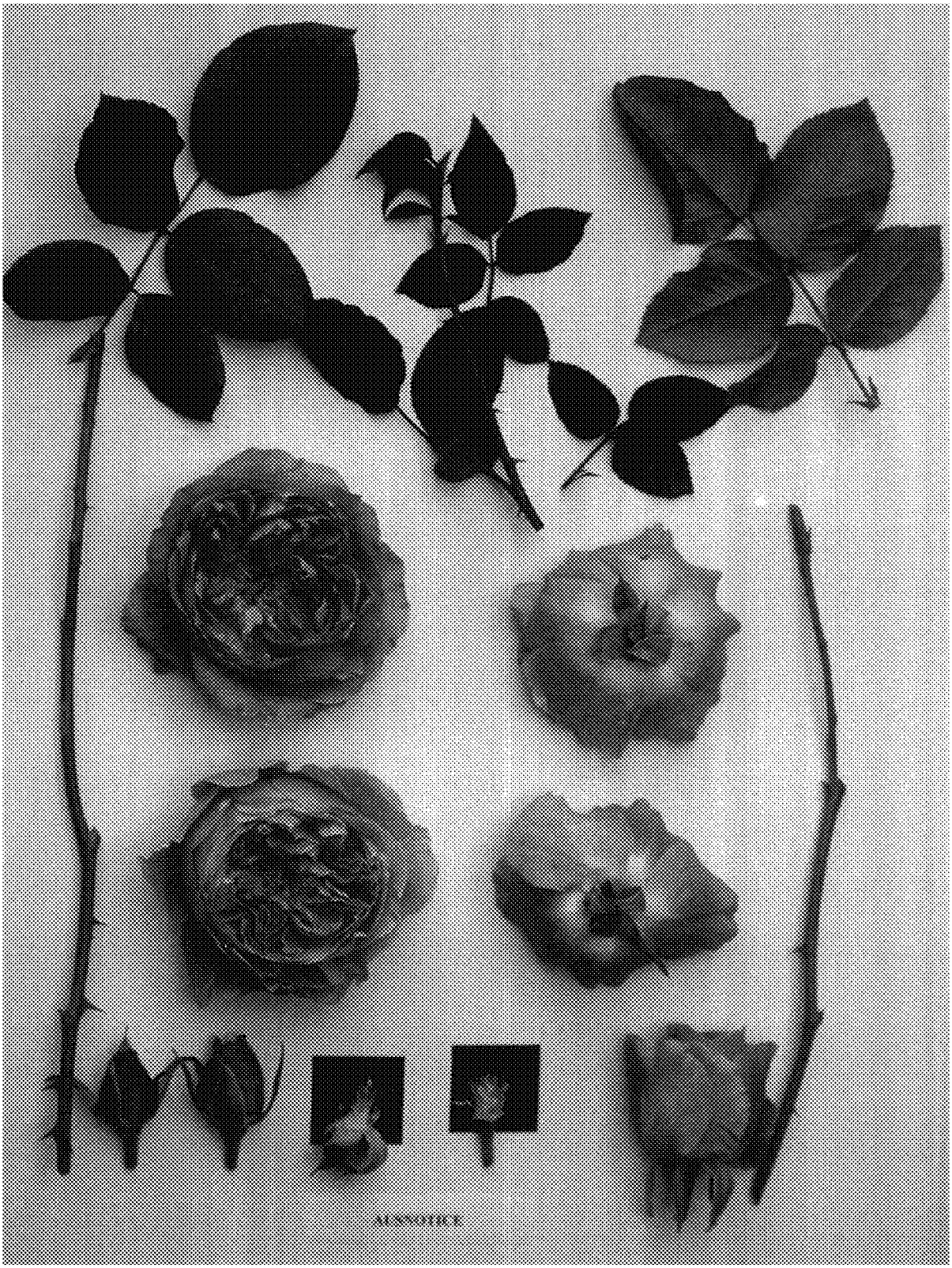

* * * * *